(12) United States Patent
Moon et al.

(10) Patent No.: US 10,801,048 B2
(45) Date of Patent: *Oct. 13, 2020

(54) METHOD OF PRODUCING L-AMINO ACIDS

(71) Applicant: CJ CHEILJEDANG CORP., Seoul (KR)

(72) Inventors: Jun Ok Moon, Seoul (KR); Sang Jo Lim, Incheon (KR); Do Hyun Kwon, Seoul (KR); Kwang Ho Lee, Seoul (KR); Hyun Won Bae, Seoul (KR)

(73) Assignee: CJ CHEILJEDANG CORP., Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 15/463,405

(22) Filed: Mar. 20, 2017

(65) Prior Publication Data
US 2017/0198316 A1   Jul. 13, 2017

Related U.S. Application Data

(63) Continuation of application No. 14/498,124, filed on Sep. 26, 2014, now Pat. No. 9,850,510.

(30) Foreign Application Priority Data

Oct. 11, 2013  (KR) .................. 10-2013-0121090
Jul. 18, 2014  (KR) .................. 10-2014-0091307

(51) Int. Cl.
| | |
|---|---|
| *C12P 13/06* | (2006.01) |
| *C12P 13/08* | (2006.01) |
| *C12P 13/12* | (2006.01) |
| *C12N 1/21* | (2006.01) |
| *C12N 15/77* | (2006.01) |
| *C12N 9/02* | (2006.01) |
| *C12N 9/04* | (2006.01) |
| *C12N 9/88* | (2006.01) |
| *C12P 13/04* | (2006.01) |
| *C12N 9/00* | (2006.01) |

(52) U.S. Cl.
CPC ............ *C12P 13/08* (2013.01); *C12N 9/0006* (2013.01); *C12N 9/0008* (2013.01); *C12N 9/88* (2013.01); *C12N 9/93* (2013.01); *C12N 15/77* (2013.01); *C12P 13/04* (2013.01); *C12Y 101/01003* (2013.01); *C12Y 102/04001* (2013.01); *C12Y 603/02013* (2013.01)

(58) Field of Classification Search
None
See application file for complete search history.

(56) References Cited

U.S. PATENT DOCUMENTS

| | | | |
|---|---|---|---|
| 5,700,661 | A | 12/1997 | Katsumata et al. |
| 5,965,391 | A | 10/1999 | Reinscheid et al. |
| 6,004,773 | A | 12/1999 | Araki et al. |
| 7,972,823 | B2 | 7/2011 | Fukui et al. |
| 2012/0021950 | A1* | 1/2012 | Greiner-Stoeffele ........................ C12N 15/1082 506/11 |
| 2014/0356518 | A1 | 12/2014 | Park et al. |
| 2015/0104837 | A1* | 4/2015 | Ha ........................ C07K 14/34 435/115 |

FOREIGN PATENT DOCUMENTS

| | | |
|---|---|---|
| JP | 10215883 A | 8/1998 |
| JP | 2005006564 A | 1/2005 |
| KR | 100073610 B1 | 5/1994 |
| KR | 100159812 B1 | 8/1998 |
| KR | 1020020066662 A | 8/2002 |
| KR | 1020080025355 A | 3/2008 |
| KR | 1020120108040 A | 10/2012 |
| KR | 1020130061570 A | 6/2013 |
| KR | 101335853 B1 | 11/2013 |
| WO | 8801645 A1 | 3/1988 |
| WO | 9523864 A1 | 9/1995 |
| WO | 200240679 A2 | 5/2002 |
| WO | 2006071099 A1 | 7/2006 |
| WO | 2013052914 A2 | 4/2013 |

OTHER PUBLICATIONS

Van Ooyen et al., Improved L-Lysine Production with Corynebacterium glutamicum and Systemic Insight Into Citrate Synthase Flux and Activity, Biotech. Bioeng., 2012, 109, 2070-81.*
Radmacher et al., Linking Central Metabolism with Increased Pathway Flux: L-Valine Accumulation by Corynebacterium glutamicum, Appl. Environ. Microbiol., 2002, 68, 2246-50.*
Binder, et al., A high-throughput approach to identify genomic variants of bacterial metabolite producers at the single-cell level, Genome Biology 2012, 13:R40, pp. 1-12.
Blombach, et al., Effect of pyruvate dehydrogenase complex deficiency on L-lysine production with Corynebacterium glutamicum, Appl Microbiol Biotechnol (2007) 76: pp. 615-623.
Extended European Search Report for Application No. 14186238.3-1410 dated Mar. 12, 2015.
Final Office Action dated Mar. 21, 2016.
GenBank, Accession No. X75504, 2005, www.ncbi.nlm.nih.gov.
Gerhardt, et al., Manual of Methods for General Bacteriology, American Society for Microbiology, (Washington, DC 20006 1981), Table of Contents.
Gerstmeir, et al., Acetate metabolism and its regulation in Corynebacterium glutamicum, Journal of Biotechnology 104 (2003), pp. 99-122.
Han, K-S, et al., The molecular structure of the Corynebacterium glutamicum threonine synthase gene, Mol. Microbiol, (1990) 4(10): 693-1702.
Hidetaka Ogino, et al., "DivS, a novel SOS-inducible cell-division suppressor in Corynebacterium glutamicum", Molecular Microbiology (2008) 67, 597-608.

(Continued)

*Primary Examiner* — Robert B Mondesi
*Assistant Examiner* — Todd M Epstein
(74) *Attorney, Agent, or Firm* — Cantor Colburn LLP

(57) ABSTRACT

Provided is a method of producing L-amino acids by using a recombinant coryneform microorganism in which the expression of a target gene is weakened by using a gene transcription inhibition method.

7 Claims, 2 Drawing Sheets

Specification includes a Sequence Listing.

(56) References Cited

OTHER PUBLICATIONS

Krylov, et al., Conditional Silencing of the *Escherichia coli* pykF Gene Results from Artificial Convergent Transcription Protected from Rho-Dependent Termination, J Mol Microbiol Biotechnol 2010; 18; pp. 1-13.
Mateos, et al., Transcriptional Analysis and Regulatory Signals of the hom-thrB Cluster of Brevibacterium lactofermentum, Journal of Bacteriology, vol. 176, No. 23, Dec. 1994, pp. 7362-7371.
NFOA, Issued Sep. 20, 2016.
Non-Final office Action dated Aug. 19, 2015.
Oliver Kirchner, et al., "Tools for genetic engineering in the amino acid-producing bacterium Corynebacterium glutamicum", Journal of Biotechnology 104 (2003) 287-299.
Patek, et al., Identification and transcriptional analysis of the dapB-ORF2-dapA-ORF4 operon of Corynebacterium glutamicum, encoding two enzymes involed in L-lysine synthesis, Biotechnolgy Letters, vol. 19, No. 11, Nov. 1997, pp. 1113-1117.
Van der Rest, et al., A heat shock following electroporation induces highly efficient transformation of Corynebacterium glutamicum with xenogeneic plasmid DNA, Appl Microbiol Biotechnol (1999) 52: pp. 541-545.
Zhang Li et al., Effect of dapA gene deletion on L-threonine production by *Escherichia coli*, 2011, p. 151-156, Journal of Gansu Agricultural University.
Dieter J. Reinscheid et al., Characterization of the Isocitrate Lyase Gene from Corynebacterium glutamicum and Biochemical Analysis of the Enzyme, 1994, pp. 3474-3483, 176, 12, American Society for Microbiology.
Dieter J. Reinscheid et al., Cloning, sequence analysis, expression and inactivation of the Corynebacterium glutamicum pta-ack operon encoding phosphotransacetylase and acetate kinase, 1999, pp. 503-513, 145, Microbiology.
Rao Zhiming et al., Disruption of hom Gene Encoding for Homoserine Dehydrogenase of Corynebacterium glutamicum, Jan. 25, 2017, p. 59-63, 27, 1, China Biotechnology.
Chinese Office Action for Application No. 201410654216.X dated Apr. 13, 2017.
Alexander Kern, et al., "Engineering primary metabolic pathways of industrial micro-organisms", Journal of Biotechnology 129 (2007) 6-29.
Eggeling, L. et al., Improved L-lysine yield with Corynebacterium glutamicum: use of dapA resulting in increased flux combined with growth limitation, Appl. Microbiol. Biotechnol., 1998, vol. 49, p. 24-30.
Ly, Y. et al., Effect of MetX and DapA Gene Knockout on Threonine Biosynthesis in Corynebacterium gltamicum, Biotechnology Bulletin, 2011, p. 158-164. (English abstract).
Eggeling, L. et al., Intracellular metabolite determination in single bacteria for HT-screening, New Biotechnology, 2012, vol. 295, S103, Poster 1.5.67.
Binder, S. et al., Nanosensors for single cell isolation of small molecule producing bacteria, New Biotechnology, Sep. 2012, vol. 295, S73, Poster 1.3.59.

\* cited by examiner

SEQUENCE LISTING

```
<160> NUMBER OF SEQ ID NOS: 36

<210> SEQ ID NO 1
<211> LENGTH: 522
<212> TYPE: DNA
<213> ORGANISM: Corynebacterium glutamicum
<220> FEATURE:
<221> NAME/KEY: gene
<222> LOCATION: (1)..(486)
<223> OTHER INFORMATION: aceA

<400> SEQUENCE: 1
agcactctga ctacctctgg aatctaggtg ccactcttct ttcgatttca acccttatcg     60
tgtttggcga tgtgatcaga ctaagtgatc accgtcacca gcaaaagggg tttgcgaact    120
ttactaagtc attaccccg  cctaaccccg acttttatct aggtcacacc ttcgaaacct    180
acggaacgtt gcggtgcctg catttcca   tttcagagca tttgcccagt acatccgtac    240
tagcaactcc cccgcccact tttctgcga  agccagaact ttgcaaactt cacaacaggg    300
gtgaccaccc ccgcacaaaa cttaaaaacc caaaccgatt gacgcaccaa tgcccgatgg    360
agcaatgtgt gaaccacgcc accacgcaaa ccgatgcaca tcacgtcgaa acagtgacag    420
tgcattagct catactttgt ggtcggcacc gcccattgcg aatcagcact taaggaagtg    480
actttgatgt caaacgttgg aaagccacgt accgcacagg aa                      522

<210> SEQ ID NO 2
<211> LENGTH: 340
<212> TYPE: DNA
<213> ORGANISM: Corynebacterium glutamicum
<220> FEATURE:
<221> NAME/KEY: gene
<222> LOCATION: (1)..(340)
<223> OTHER INFORMATION: pta

<400> SEQUENCE: 2
ctttgctggg gtcagatttg tcacgctgcg cgctttcata gacccatta  atgggggtg      60 aagagctgta aagtaccgct aaaaactttg caaagggtgc ttcgcaactt gtaaccgctc    120
cgtattgttt tctacggcaa taagcatttg tgctgctcaa agcgtggaat tgagatcggt    180
ttgaaaatta caaaataaaa ctttgcaaac cgggctgtac gcaaggcgga cgaacgctaa    240
actatgtaag aaatcacaac ctcccctcat tagtgccagg aggcacaagc ctgaagtgtc    300
atcaatgaga aggttcaggc tgaaattaga aaggcgatgt                          340
```

```
<210> SEQ ID NO 3
<211> LENGTH: 35
<212> TYPE: DNA
<213> ORGANISM: Artificial Sequence
<220> FEATURE:
<223> OTHER INFORMATION: aceE P1F

<400> SEQUENCE: 3
ccggggatcc tctagacctc cggcccatac gttgc                                   35

<210> SEQ ID NO 4
<211> LENGTH: 30
<212> TYPE: DNA
<213> ORGANISM: Artificial Sequence
<220> FEATURE:
<223> OTHER INFORMATION: aceE P1R

<400> SEQUENCE: 4
ttgagactag ttattcctca ggagcgtttg                                         30

<210> SEQ ID NO 5
<211> LENGTH: 30
<212> TYPE: DNA
<213> ORGANISM: Artificial Sequence
<220> FEATURE:
<223> OTHER INFORMATION: aceE P2F

<400> SEQUENCE: 5
gaataactag tctcaaggga cagataaatc                                         30

<210> SEQ ID NO 6
<211> LENGTH: 36
<212> TYPE: DNA
<213> ORGANISM: Artificial Sequence
<220> FEATURE:
<223> OTHER INFORMATION: aceE P2R

<400> SEQUENCE: 6
gcaggtcgac tctagagacc gaaaagatcg tggcag                                  36

<210> SEQ ID NO 7
<211> LENGTH: 35
<212> TYPE: DNA
<213> ORGANISM: Artificial Sequence
<220> FEATURE:
<223> OTHER INFORMATION: PaceA P3F

<400> SEQUENCE: 7
gtcccttgag actagtagca ctctgactac ctctg                                   35

<210> SEQ ID NO 8
<211> LENGTH: 35
<212> TYPE: DNA
<213> ORGANISM: Artificial Sequence
<220> FEATURE:
<223> OTHER INFORMATION: PaceA P3R

<400> SEQUENCE: 8
ctgaggaata actagtttcc tgtgcggtac gtggc                                   35

<210> SEQ ID NO 9
<211> LENGTH: 35
<212> TYPE: DNA
<213> ORGANISM: Artificial Sequence
<220> FEATURE:
<223> OTHER INFORMATION: aceE P4F
```

<400> SEQUENCE: 9
ccggggatcc tctagaggtc ccaggcgact acacc					35

<210> SEQ ID NO 10
<211> LENGTH: 35
<212> TYPE: DNA
<213> ORGANISM: Artificial Sequence
<220> FEATURE:
<223> OTHER INFORMATION: aceE P4R

<400> SEQUENCE: 10
gagctactag tacgacgaat cccgccgcca gacta					35

<210> SEQ ID NO 11
<211> LENGTH: 35
<212> TYPE: DNA
<213> ORGANISM: Artificial Sequence
<220> FEATURE:
<223> OTHER INFORMATION: aceE P5F

<400> SEQUENCE: 11
gtcgtactag tagctctttt tagccgagga acgcc					35

<210> SEQ ID NO 12
<211> LENGTH: 35
<212> TYPE: DNA
<213> ORGANISM: Artificial Sequence
<220> FEATURE:
<223> OTHER INFORMATION: aceE P5R

<400> SEQUENCE: 12
gcaggtcgac tctagacatg ctgttggatg agcac					35

<210> SEQ ID NO 13
<211> LENGTH: 35
<212> TYPE: DNA
<213> ORGANISM: Artificial Sequence
<220> FEATURE:
<223> OTHER INFORMATION: PaceA P6F

<400> SEQUENCE: 13
aaaaagagct actagtagca ctctgactac ctctg					35

<210> SEQ ID NO 14
<211> LENGTH: 35
<212> TYPE: DNA
<213> ORGANISM: Artificial Sequence
<220> FEATURE:
<223> OTHER INFORMATION: PaceA P6R

<400> SEQUENCE: 14
gattcgtcgt actagtttcc tgtgcggtac gtggc					35

<210> SEQ ID NO 15
<211> LENGTH: 36
<212> TYPE: DNA
<213> ORGANISM: Artificial Sequence
<220> FEATURE:
<223> OTHER INFORMATION: Ppta P7F

<400> SEQUENCE: 15
gtcccttgag actagtcttt gctggggtca gatttg					36

<210> SEQ ID NO 16
<211> LENGTH: 35

<210> SEQ ID NO 16
<211> LENGTH: 35
<212> TYPE: DNA
<213> ORGANISM: Artificial Sequence
<220> FEATURE:
<223> OTHER INFORMATION: Ppta P7R

<400> SEQUENCE: 16
ctgaggaata actagtacat cgcctttcta atttc        35

<210> SEQ ID NO 17
<211> LENGTH: 35
<212> TYPE: DNA
<213> ORGANISM: Artificial Sequence
<220> FEATURE:
<223> OTHER INFORMATION: hom h1F

<400> SEQUENCE: 17
ccggggatcc tctagaccag gtgagtccac ctacg        35

<210> SEQ ID NO 18
<211> LENGTH: 35
<212> TYPE: DNA
<213> ORGANISM: Artificial Sequence
<220> FEATURE:
<223> OTHER INFORMATION: hom h1R

<400> SEQUENCE: 18
gaggcggatc actagtttag tccctttcga ggcgg        35

<210> SEQ ID NO 19
<211> LENGTH: 25
<212> TYPE: DNA
<213> ORGANISM: Artificial Sequence
<220> FEATURE:
<223> OTHER INFORMATION: hom h2F

<400> SEQUENCE: 19
actagtgatc cgcctcgaaa gggac        25

<210> SEQ ID NO 20
<211> LENGTH: 36
<212> TYPE: DNA
<213> ORGANISM: Artificial Sequence
<220> FEATURE:
<223> OTHER INFORMATION: hom h2R

<400> SEQUENCE: 20
gcaggtcgac tctagagact gcggaatgtt gttgtg        36

<210> SEQ ID NO 21
<211> LENGTH: 35
<212> TYPE: DNA
<213> ORGANISM: Artificial Sequence
<220> FEATURE:
<223> OTHER INFORMATION: PaceA h3F

<400> SEQUENCE: 21
gaggcggatc actagtagca ctctgactac ctctg        35

<210> SEQ ID NO 22
<211> LENGTH: 35
<212> TYPE: DNA
<213> ORGANISM: Artificial Sequence
<220> FEATURE:
<223> OTHER INFORMATION: PaceA h3R

<400> SEQUENCE: 22
aagggactaa actagtttcc tgtgcggtac gtggc                          35

<210> SEQ ID NO 23
<211> LENGTH: 35
<212> TYPE: DNA
<213> ORGANISM: Artificial Sequence
<220> FEATURE:
<223> OTHER INFORMATION: mur m1F

<400> SEQUENCE: 23
ccggggatcc tctagaaacc ctcgttcaga ggtgc                          35

<210> SEQ ID NO 24
<211> LENGTH: 37
<212> TYPE: DNA
<213> ORGANISM: Artificial Sequence
<220> FEATURE:
<223> OTHER INFORMATION: mur m1R

<400> SEQUENCE: 24
ttgtgatcat ctcgagctat ccttcttccg tagtaag                        37

<210> SEQ ID NO 25
<211> LENGTH: 28
<212> TYPE: DNA
<213> ORGANISM: Artificial Sequence
<220> FEATURE:
<223> OTHER INFORMATION: mur m2F

<400> SEQUENCE: 25
agctcgagat gatcacaatg acccttgg                                  28

<210> SEQ ID NO 26
<211> LENGTH: 35
<212> TYPE: DNA
<213> ORGANISM: Artificial Sequence
<220> FEATURE:
<223> OTHER INFORMATION: mur m2R

<400> SEQUENCE: 26
gcaggtcgac tctagacatg agcataaatg tcagc                          35

<210> SEQ ID NO 27
<211> LENGTH: 27
<212> TYPE: DNA
<213> ORGANISM: Artificial Sequence
<220> FEATURE:
<223> OTHER INFORMATION: mur m3F

<400> SEQUENCE: 27
tcatcagcag cactctgact acctctg                                   27

<210> SEQ ID NO 28
<211> LENGTH: 35
<212> TYPE: DNA
<213> ORGANISM: Artificial Sequence
<220> FEATURE:
<223> OTHER INFORMATION: mur m3R

<400> SEQUENCE: 28
agaaggatag ctcgagttcc tgtgcggtac gtggc                          35

<210> SEQ ID NO 29
<211> LENGTH: 27
<212> TYPE: DNA
<213> ORGANISM: Artificial Sequence
<220> FEATURE:
<223> OTHER INFORMATION: mur m4F

<400> SEQUENCE: 29
agagtgctgc tgatgatcct cgatttg    27

<210> SEQ ID NO 30
<211> LENGTH: 36
<212> TYPE: DNA
<213> ORGANISM: Artificial Sequence
<220> FEATURE:
<223> OTHER INFORMATION: mur m4R

<400> SEQUENCE: 30
ttgtgatcat ctcgagggtt ttctctcctc cacagg    36

<210> SEQ ID NO 31
<211> LENGTH: 35
<212> TYPE: DNA
<213> ORGANISM: Artificial Sequence
<220> FEATURE:
<223> OTHER INFORMATION: dapA d1F

<400> SEQUENCE: 31
ccggggatcc tctagatgtt tggcttgctt tgggc    35

<210> SEQ ID NO 32
<211> LENGTH: 32
<212> TYPE: DNA
<213> ORGANISM: Artificial Sequence
<220> FEATURE:
<223> OTHER INFORMATION: dapA d1R

<400> SEQUENCE: 32
gttgatgcac tagtttatag aactccagct tt    32

<210> SEQ ID NO 33
<211> LENGTH: 33
<212> TYPE: DNA
<213> ORGANISM: Artificial Sequence
<220> FEATURE:
<223> OTHER INFORMATION: dapA d2F

<400> SEQUENCE: 33
ttctataaac tagtgcatca acgtaggaga tcc    33

<210> SEQ ID NO 34
<211> LENGTH: 34
<212> TYPE: DNA
<213> ORGANISM: Artificial Sequence
<220> FEATURE:
<223> OTHER INFORMATION: dapA d2R

<400> SEQUENCE: 34
gcaggtcgac tctagacgtt ctgggaaccc tgag    34

<210> SEQ ID NO 35
<211> LENGTH: 35
<212> TYPE: DNA
<213> ORGANISM: Artificial Sequence
<220> FEATURE:
<223> OTHER INFORMATION: PaceA d3F

<400> SEQUENCE: 35
acgttgatgc actagtagca ctctgactac ctctg    35

```
<210> SEQ ID NO 36
<211> LENGTH: 35
<212> TYPE: DNA
<213> ORGANISM: Artificial Sequence
<220> FEATURE:
<223> OTHER INFORMATION: PaceA d3R

<400> SEQUENCE: 36
agttctataa actagtttcc tgtgcggtac gtggc                              35
```

METHOD OF PRODUCING L-AMINO ACIDS

CROSS-REFERENCE TO RELATED APPLICATIONS

This application is a continuation of U.S. application Ser. No. 14/498,124, filed Sep. 26, 2014, which claims the benefit of Korean Patent Application No. 10-2013-0121090, filed on Oct. 11, 2013, and Korean Patent Application No. 10-2014-0091307, filed on Jul. 18, 2014, in the Korean Intellectual Property Office, the disclosures of each of which are incorporated herein in their entirety by reference.

BACKGROUND

1. Field

One or more embodiments of the present invention relate to a method of producing L-amino acids by using a gene transcription inhibition method.

2. Description of the Related Art

Pyruvate, which is produced through glycolysis of various carbon sources in coryneform microorganisms, is converted into aspartate via oxaloacetate. The aspartate is converted into amino acids such as threonine, methionine, isoleucine, and lysine through various biosynthetic pathways (FIG. 1). Therefore, the expression of genes, located at each branch point in the amino acid biosynthetic processes, may be inhibited to decrease byproduct production and increase target amino acid production.

As described above, to develop a microorganism strain, which is capable of high-potency production of target materials by using genetic engineering and metabolic engineering, the expression of genes related with various metabolic processes of a microorganism needs to be selectively controlled. Recently, a technology for weakening gene expression, which is called "artificial convergent transcription," was reported (Krylov et al., J Mol Microbiol Biotechnol, 18:1-13, 2010). The artificial convergent transcription is a technology for weakening the expression of a target gene by inserting a promoter into a downstream region of a transcription terminator of the target gene so that the opposite direction of the promoter causes a collision of RNA polymerase complexes derived from each promoter during transcription.

The inventors developed a technology to selectively inhibit the expression of a target gene in the presence of acetate by inserting an acetate-inducible promoter in a direction opposite to the target gene transcription, and effectively applied the technology to inhibit the expression of genes located at branch points in a coryneform microorganism. Then the inventors verified to provide the coryneform microorganism of producing L-amino acid with high yield by using the technology and completed the present invention.

SUMMARY

The purpose of the present invention is to provide a method of producing L-amino acids by using an acetate-inducible promoter to inhibit transcription of a target gene.

One embodiment of the present invention provides a method of producing L-amino acids, the method including 1) culturing a recombinant coryneform microorganism capable of producing L-amino acids, wherein the recombinant coryneform microorganism is transformed by inserting an acetate-inducible promoter to the downstream of a stop codon of a target gene in a chromosome; and 2) adding acetate during the culturing to weaken expression of the target gene, and to strengthen the L-amino acids production capability of the recombinant coryneform microorganism.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
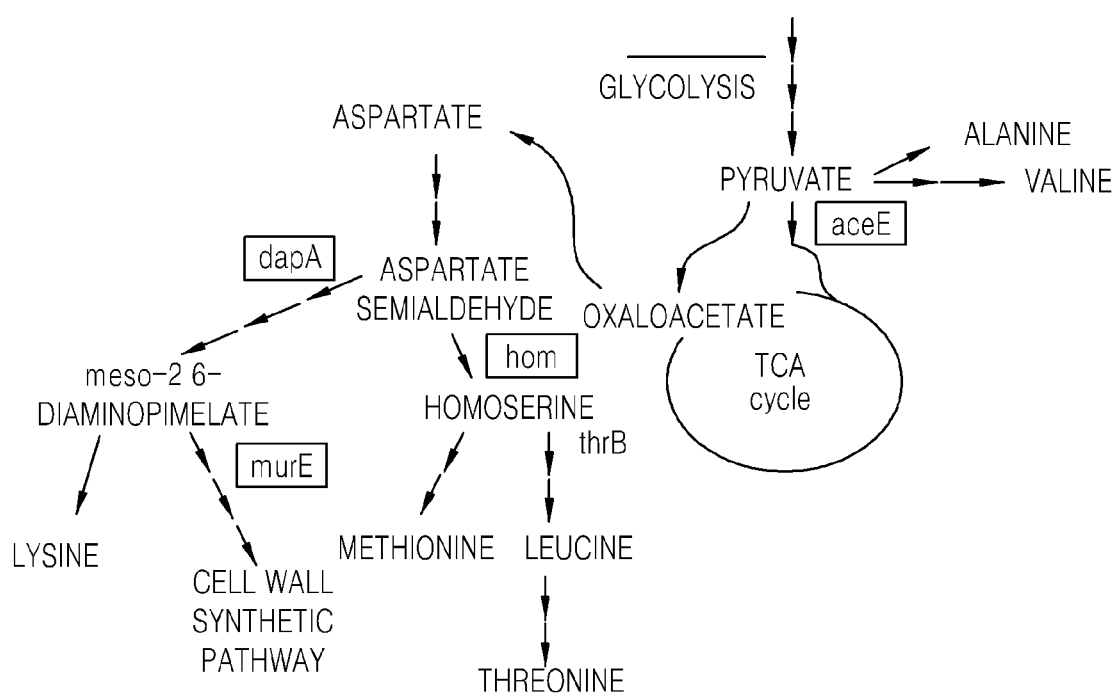
FIG. 1 shows branch points of the amino acids biosynthesis process in a coryneform microorganism.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Hereinafter, the present invention is described in detail.

One embodiment of the present invention provides a method of producing L-amino acids, the method including 1) culturing a recombinant coryneform microorganism capable of producing L-amino acids, wherein the recombinant coryneform microorganism is transformed by inserting an acetate-inducible promoter to the downstream of a stop codon of a target gene in a chromosome; and 2) adding acetate during the culturing to weaken the expression of the target gene, and to strengthen the L-amino acids production capability of the recombinant coryneform microorganism.

The term "acetate-inducible promoter" used herein refers to a promoter having gene expression-inducing activity in the presence of acetate.

In a coryneform microorganism, acetate is converted by acetate kinase (ackA, NCgl2656) and phosphotransacetylase (pta, NCgl2657), or by succinyl-CoA:acetate CoA-transferase (actA, NCgl2480), into acetyl CoA, and then metabolized by isocitrate lyase (aceA, NCgl2248) in a glyoxalate cycle. In Escherichia coli, acetate is converted into acetyl CoA by acetyl-CoA synthetase (acs, b4069) (Gerstmeir et al., J Biotechnol, 104:99-122, 2003). The expression of the mentioned genes involved in the acetate metabolism is induced in the presence of acetate. Therefore, when the promoters of the genes are used, the expression of the gene may be specifically induced in the presence of acetate.

Acetate-inducible promoters include a promoter of a gene encoding isocitrate lyase (aceA, NCgl2248) or a promoter of an operon of a gene encoding acetate kinase (ackA, NCgl2656) and a gene encoding phosphotransacetylase (pta, NCgl2657), which is an upstream promoter of the pta gene. More specifically, among the acetate-inducible promoters described above, the promoter of the aceA gene is represented by nucleotide sequence of SEQ ID NO: 1 and includes 486 base pairs in the upstream of the aceA gene and 36 base pairs from an N-terminal of an open reading frame (ORF).

The upstream promoter of the pta gene, which is another acetate-inducible promoter, is represented by nucleotide sequence of SEQ ID NO: 2 and includes 340 base pairs in the upstream of the pta gene.

In addition, it is obvious that any promoter capable of inducing a target gene expression by acetate may be included in the scope of the present invention. For example, the acetate-inducible promoters may include a nucleotide sequence including the nucleotide sequence of SEQ ID NO: 1 or 2, or including a conserved sequence of the nucleotide sequence of SEQ ID NO: 1 or 2, and one or a plurality of nucleotides (specifically 2 to 20, more specifically, 2 to 10, further more specifically, 2 to 5 nucleotides, depending on the steric conformation of amino acid residues of a protein) that are substituted, deleted, inserted, added, or inversed at one or more locations. As long as the function of the inducible promoter is maintained or strengthened, it may include a nucleotide sequence has more than 80% homology with the nucleotide sequence of SEQ ID NO: 1 or 2, specifically by more than 90%, more sepecifically by more than 95%, further more specifically by more than 97%. As long as the function of the inducible promoter is maintained, the substituted, deleted, inserted, added, or inversed nucleotide sequence may include a spontaneous mutant sequence or even an artificial mutant sequence.

The term "homology" used herein refers to the identity between two different nucleotide sequences. Homology may be determined by a method known in this art by using a BLAST 2.0 software program which calculates such parameters as score, identity, and similarity. However, the method of determining homology is not limited thereto.

Unless mentioned otherwise herein, the term "upstream" refers to a 5' direction, and the term "downstream" refers to a 3' direction. Usually, the direction of the transcription proceeding is 5' to 3', so that the promoter position is usually the upstream (5') of the target gene.

Herein, a target gene in a chromosome may be a gene involved in a process of biologically synthesizing amino acids such as threonine, methionine, isoleucine, and lysine from various carbon sources, especially a gene located at a branch point of a biosynthetic pathway.

For example, with respect to lysine, a pyruvate dehydrogenase subunit E1 (aceE, NCgl2167) gene which is involved in the conversion of pyruvate into acetyl CoA, a homoserine dehydrogenase (hom, NCgl1136) gene which produces homoserine from aspartate, and a UDP-N-acetylmuramoylalanyl-D-glutamate-2,6-diaminopimelate ligase (murE, NCgl2083) gene which uses meso-2,6-diaminopimelate that is a precursor of lysine in somatic synthesis, are located at branch points of the biosynthetic pathway.

In addition, a dihydrodipicolinate synthase (dapA, NCgl1896) gene involved in producing lysine from aspartate is at a branch point with respect to threonine, and a homoserine kinase (thrB, NCgl1137) gene involved in producing threonine from homoserine is at a branch point with respect to methionine. With respect to alanine and valine that are pyruvate-derived amino acids, a pyruvate dehydrogenase subunit E1 (aceE, NCgl2167) gene involved in the conversion of pyruvate into acetyl CoA is at a branch point.

Therefore, a target gene may be selected from the group consisting of a gene encoding a pyruvate dehydrogenase subunit E1 (aceE, NCgl2167), a gene encoding homoserine dehydrogenase (hom, NCgl1136), a gene encoding a UDP-N-acetylmuramoylalanyl-D-glutamate-2,6-diaminopimelate ligase (murE, NCgl2083), and a gene encoding dihydrodipicolinate synthase (dapA, NCgl1896), but is not limited thereto.

Specifically, the pyruvate dehydrogenase subunit E1 (aceE, NCgl2167) is one of the protein subunits of pyruvate dehydrogenase complex (PDHC), which is involved in the inflow of pyruvate that is a final metabolite of glycolysis to a tricarboxylic acid cycle (TCA cycle). Therefore, weakening the expression of the aceE gene may decrease the inflow of carbon sources to a TCA cycle and increase the inflow of carbon sources to a lysine biosynthetic pathway to increase lysine production.

Homoserine dehydrogenase (hom, NCgl1136) is an enzyme synthesizing homoserine from aspartate semialdehyde. Since aspartate semialdehyde is one of the intermediate precursors of a lysine biosynthetic pathway, weakening the hom gene activity may decrease the inflow of carbon sources to a homoserine biosynthetic pathway and increase the inflow of carbon sources to a lysine biosynthetic pathway to increase lysine production.

UDP-N-acetylmuramoylalanyl-D-glutamate-2,6-diaminopimelate ligase (murE, NCgl2083) uses meso-2,6-diaminopimelate for somatic synthesis. Since meso-2,6-diaminopimelate is also used as a precursor for lysine biosynthesis, weakening of the murE gene activity may decrease the inflow of carbon sources to somatic synthesis and increase the inflow of carbon sources to a lysine biosynthetic pathway to increase lysine production.

Dihydrodipicolinate synthase (dapA, NCgl1896) is an enzyme which is involved in lysine production by using aspartate semialdehyde. Since aspartate semialdehyde is one of the intermediate precursors of a lysine biosynthetic pathway, weakening of the dapA gene activity may decrease the inflow of carbon sources to lysine biosynthetic pathway and increase the inflow of carbon sources to a threonine biosynthetic pathway to increase threonine production.

The term "stop codon" used herein refers to codons that do not encode an amino acid on mRNA, but operate as a signal for termination of protein synthesis. Three codons including UAA, UAG, and UGA are used conventionally as stop codons.

The term "transcription terminator" used herein refers to an GC base-rich inverted repeat sequence. A transcription terminator forms a hairpin loop to terminate gene transcription.

In the present invention, to weaken the expression of a target gene, as described above, an acetate-inducible promoter may be introduced to a downstream of a stop codon of a target gene, specifically, between a stop codon and an upstream of a transcription terminator. An acetate-inducible promoter may be used to cause an inverse transcription of a target gene so that RNA polymerase complexes may conflict with each other to weaken the expression of a target gene.

The expression of a target gene may be weakened any time of culturing. More specifically the expression of a target gene may be weakened before or during culturing.

The term "transformation" used herein refers to introducing a vector including a polynucleotide which encodes a target gene into a host cell so that a protein encoded by the polynucleotide may be expressed in the host cell. As long as an introduced polynucleotide may be expressed in a host cell, the polynucleotide may be inserted into the chromosome of the host cell or exist out of the chromosome. In addition, the polynucleotide includes DNA or RNA encoding a target protein. As long as the polynucleotide can be introduced into and expressed in a host cell, the polynucleotide may be introduced in any form.

In an embodiment of the invention, the coryneform microorganism may include microorganisms of genus *Corynebacterium*, genus *Brevibacterium*, genus *Arthrobacter sp.*, and genus *Microbacterium sp*. Examples of the coryneform microorganism include *Corynebacterium glutamicum, Corynebacterium thermoaminogenes, Brevibacterium flavum, Brevibacterium lactofermentum*, and L-amino acid-producing variants prepared therefrom. Specifically, the coryneform microorganism may be *Corynebacterium glutamicum*, but is not limited to these examples.

More specifically, the coryneform microorganisms in the present invention may include *Corynebacterium glutamicum* KCCM11016P (Former Accession NO: KFCC10881, Refer to Korean Patent NO: 10-0159812), *Corynebacterium glutamicum* KCCM10770P (Refer to Korean Patent NO: 10-0924065), and *Corynebacterium glutamicum* KCCM11347P (Former Accession NO: KFCC10750, Refer to Korean Patent NO: 10-0073610).

*Corynebacterium glutamicum* CJ3P may be also included the the coryneform microorganisms in the present invention. CJ3P has been developed to have lysine-producing capability by introducing mutation to three genes involved in lysine-producing efficiency (pyc(P458S), hom(V59A), and lysC(T311I)) to a parent strain, a wild type *Corynebacterium glutamicum* (ATCC13032) according to the report by Binder et al. (Binder et al., Genome Biology, 13:R40, 2012).

In addition, another coryneform microorganism in the present invention may be *Corynebacterium glutamicum* KCCM11222P, which is an L-threonine-producing strain (Refer to Korean Patent NO: 10-1335853).

According one embodiment of the present invention, in all the coryneform microorganisms to which a promoter being represented by nucleotide sequence of SEQ ID NO: 1 or SEQ ID NO: 2 was introduced, the L-lysine or L-threonine productivity was increased compared to that of the parent strain.

With respect to the method provided in the present invention, culturing of a coryneform microorganism may be performed by applying any culturing conditions and culturing method known in this art.

A culture medium, which may be used in culturing of a coryneform strain, may be, for example, the culture mediums described in Manual of Methods for General Bacteriology by the American Society for Bacteriology (Washington D.C., USA, 1981).

The carbon sources, which may be used in the culture medium, may include a carbohydrate such as glucose, saccharose, lactose, fructose, maltose, starch, and cellulose, an oil or lipid such as soybean oil, sunflower oil, castor oil, and coconut oil, a fatty acid such as palmitic acid, stearic acid, and linoleic acid, an alcohol such as glycerol and ethanol, and an organic acid such as acetic acid. These substances may be individually or as a mixture.

The nitrogen sources, which may be used in the culture medium, may include peptone, yeast extract, beef extract, malt extract, corn steep liquid, soybean, and urea, and an inorganic nitrogen source such as ammonium sulfate, ammonium chloride, ammonium phosphate, ammonium carbonate, and ammonium nitrate. These nitrogen sources also may be individually or as a mixture.

The phosphorous sources, which may be used in the culture medium, may include potassium dihydrogen phosphate, dipotassium hydrogen phosphate, and a sodium-containing salt thereof. In addition, a culture medium may have to include a metal salt such as magnesium sulfate and iron sulfate needed for growth. Beside the substances described above, necessary substances for growth such as amino acids and vitamins may be used. In addition, appropriate precursors may be used in a culture medium. The raw materials may be added to the culture solution in a batch mode or a continuous mode during the culturing.

During the culturing of the microorganism, the pH of the culture medium may be adjusted by adding a basic compound such as ammonium hydroxide, potassium hydroxide, and ammonia, or an acidic compound such as phosphoric acid and sulfuric acid to the culture medium in an appropriate mode. In addition, bubble formation may be repressed by using an anti-forming agent such as fatty acid polyglycol ester. To maintain aerobic conditions, oxygen or an oxygen-containing gas (for example, air) may be injected to the culture medium. The temperature of the culture medium may be usually from about 20° C. to about 45° C., specifically, from about 25° C. to about 40° C. The culturing may continue until a desired amount of an L-amino acid is produced, but an appropriate culturing time may be from about 10 to 160 hours.

With respect to the method provided in the present invention, culturing may be performed in a continuous mode or a batch mode such as a batch process, a fed-batch process, and a repeated fed-batch process. These culturing methods are known in the art, and any of the culturing methods may be used.

The term "culturing" used herein may include both preparing a culture medium and the time during growing the microorganisms.

With respect to the method provided in the present invention, the method may include further purifying or recovering step. A target L-amino acid may be purified or recovered from a culture solution by using an appropriate method known in this art according to the method such as batch culturing, continuous culturing, and fed-batch culturing.

An L-amino acid produced in the culturing of the present invention may be one selected from the group consisting of threonine, methionine, isoleucine, lysine, valine, and alanine, specifically, lysine or threonine.

Hereinafter, the present invention will be described in further detail with reference to examples. These examples are illustrative purposes only and the scope of the present invention is not limited thereto.

EXAMPLES

Example 1: Selection of Acetate-Inducible Promoter

Isocitrate lyase (aceA, NCgl2248) is a key enzyme of a glyoxylate cycle, and a gene encoding isocitrate lyase is expressed in the presence of acetate. In addition, acetate kinase (ackA, NCgl2656) and phosphotransacetylase (pta, NCgl2657), which are enzymes that are involved in an acetate metabolic process, form an operon, and the expression thereof is strengthened in the presence of acetate. The promoter regions of the aceA gene and the pta-ackA operon are already known (Gerstmeir et al., J Biotechnol, 104, 99-122, 2003).

In Example 1, a promoter of the aceA gene and a promoter of the pta-ack operon that is an upstream promoter region of the pta gene were selected to inhibit the transcription of a target gene in the presence of acetate. Based on the aceA gene registered in the US NIH GenBank (NCBI Registration NO: NCgl2248), a nucleotide sequence (SEQ ID NO: 1), including 486 base pairs in the upstream of the aceA gene and 36 base pairs from an N-terminal of an open reading frame (ORF), was obtained. In addition, Based on the pta gene registered in the US NIH GenBank (NCBI Registration NO: NCgl2657), a nucleotide sequence (SEQ ID NO: 2), including 340 base pairs in the upstream of the pta gene, was obtained.

Example 2: Preparation of Vector for Inhibiting aceE Gene Expression

A pyruvate dehydrogenase subunit E1 (aceE, NCgl2167) is one of the protein subunits of pyruvate dehydrogenase complex (PDHC), which is involved in inflowing pyruvate that is a final metabolite of glycolysis to a TCA cycle. Therefore, weakening the expression of the aceE gene may decrease the inflow of carbon sources to a TCA cycle and increase the inflow of carbon sources to a lysine biosynthetic pathway to increase lysine production (Blombach et al., Appl Microbiol Biotechnol, 76(3):615-23, 2007).

Figure 2A:
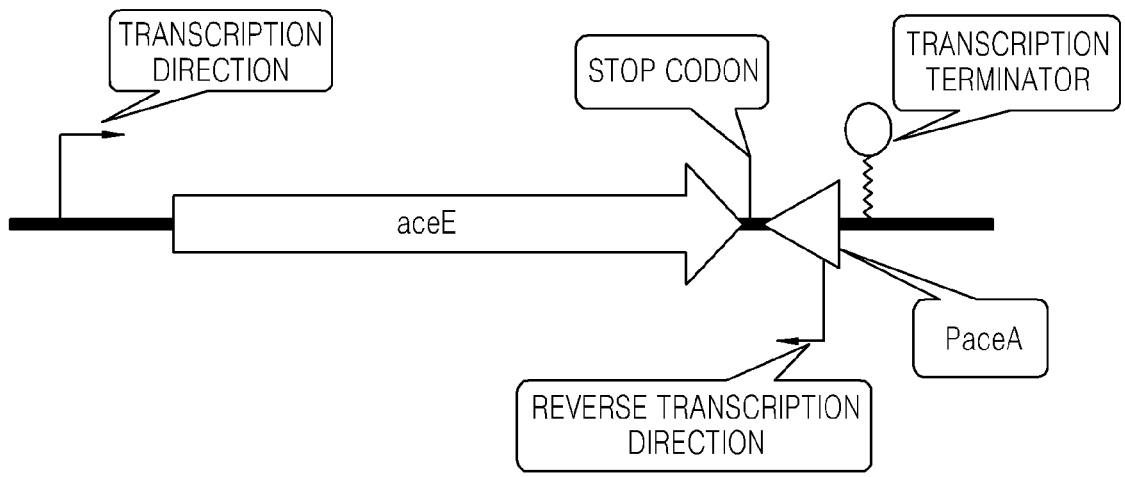
FIG. 2A is a schematic diagram showing inhibition of aceE gene expression by inserting an aceA gene promoter between the stop codon and the transcription terminator upstream of the aceE gene in a direction opposite to the direction of the aceE gene transcription.
Figure 2B:
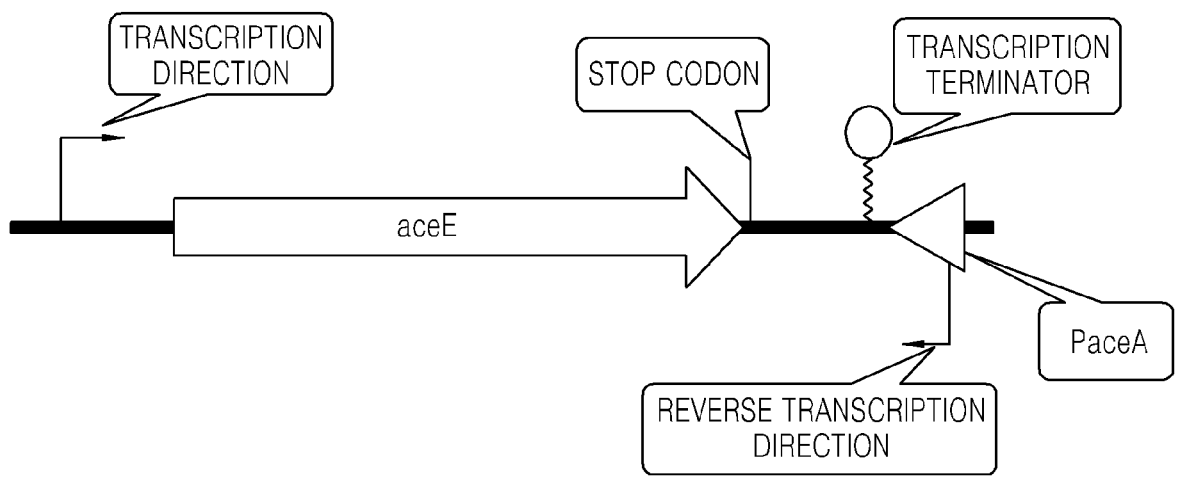
FIG. 2B is a schematic diagram showing inhibition of aceE gene expression by inserting an aceA gene promoter to the downstream of the transcription terminator in a direction opposite to the direction of the aceE gene transcription.

The aceA gene promoter was inserted to the downstream of the aceE gene so that the transcription from this promoter may occur in a direction opposite to the original direction of the aceE gene transcription to inhibit the expression of the aceE gene selectively in the presence of acetate (FIG. 2).

Firstly, CLC main workbench software (CLC Bio, Denmark) was used to predict a transcription terminator of the aceE gene. A transcription terminator is a GC base-rich inverted repeat sequence and forms a hairpin loop to terminate gene transcription. The result of predicting a transcription terminator of the aceE gene showed that 36 base pairs, from the 21st base pair to the 56th base pair in the downstream from the stop codon of the aceE gene, form a hairpin loop as a transcription terminator. Based on this result, two vectors were prepared to insert aceE promoter into either the upstream or the downstream, respectively, of the transcription terminator of aceE gene so that the transcription from the this promoter may occur in a opposite direction of the original one.

<2-1> Preparation of pDZ-aceE1-PaceA Vector for Inhibiting aceE Gene Expression

A vector was prepared by inserting an aceA gene promoter to the downstream of the aceE gene stop codon, which is between the stop codon and the upstream of the transcription terminator.

To obtain a fragment of a *Corynebacterium glutamicum*-derived aceE gene, the chromosomal DNA of *Corynebacterium glutamicum* KCCM11016P was used as a template to synthesize primers (SEQ ID NOs: 3 and 4), which were designed to have an XbaI restriction enzyme recognition site at a 5' end of the fragment and an SpeI restriction enzyme recognition site at a 3' end of the fragment. A PCR was performed by using the synthesized primers to obtain a DNA fragment including 296 base pairs between the 2474th nucleotide from the start codon of aceE gene and the 2769th nucleotide, a stop codon of aceE gene. In addition, primers (SEQ ID NOs: 5 and 6), which were designed to have an SpeI recognition site at a 5' end of the fragment and an XbaI recognition site at a 3' end of the fragment were synthesized, and a PCR was performed by using the primers to obtain a DNA fragment including 300 base pairs in the downstream of the aceE gene stop codon. PfuUltra™ High-Fidelity DNA Polymerase (Stratagene) was used as a polymerase, and a PCR was performed with 30 cycles of denaturing at 95° C. for 30 seconds; annealing at 55° C. for 30 seconds; and polymerization at 72° C. for 30 seconds and then polymerization at 72° C. for 7 minutes.

The two PCR amplification products and a pDZ vector (Refer to Korean Patent NO: 10-0924065) for chromosomal introduction that had already been prepared by cleaving with an XbaI restriction enzyme were cloned by using an In-fusion Cloning Kit (TAKARA, JP) to prepare a pDZ-aceE1 vector.

```
SEQ ID NO: 3: aceE-P1F
5'-ccgggggatcctctagacctccggcccatacgttgc-3'

SEQ ID NO: 4: aceE-P1R
5'-ttgagactagttattcctcaggagcgtttg-3'

SEQ ID NO: 5: aceE-P2F
5'-gaataactagtctcaagggacagataaatc-3'

SEQ ID NO: 6: aceE-P2R
5'-gcaggtcgactctagagaccgaaaagatcgtggcag-3'
```

To obtain a promoter fragment of a *Corynebacterium glutamicum*-derived aceA gene, primers which were designed to have an SpeI restriction enzyme recognition site at a 5' end and at a 3' end of the fragment (SEQ ID NOs: 7 and 8) were synthesized. The PCR was performed using the chromosomal DNA of *Corynebacterium glutamicum* KCCM11016P as a template and the synthesized primers to amplify a promoter region of about 500 base pairs being represented by a nucleotide sequence of SEQ ID NO: 1. The PCR amplification product and a DNA fragment that was obtained by treating a pDZ-aceE1 with SpeI restriction enzyme were cloned by using an In-fusion Cloning Kit (TAKARA, JP) to prepare a pDZ-aceE1-PaceA vector.

```
SEQ ID NO: 7: PaceA-P3F
5'-gtcccttgagactagtagcactctgactacctctg-3'

SEQ ID NO: 8: PaceA-P3R
5'-ctgaggaata actagtttcctgtgcggtacgtggc-3'
```

<2-2> Preparation of pDZ-aceE2-PaceA Vector for Inhibiting aceE Gene Expression

A vector was prepared by inserting an aceA gene promoter to the downstream of the aceE gene transcription terminator.

To obtain a fragment of a *Corynebacterium glutamicum*-derived aceE gene, the chromosomal DNA of *Corynebacterium glutamicum* KCCM11016P was used as a template, and primers, which were designed to have an XbaI restriction enzyme recognition site at a 5' end of the fragment and an SpeI restriction enzyme recognition site at a 3' end of the fragment (SEQ ID NOs: 9 and 10), were used. A PCR was performed by using the synthesized primers to obtain a DNA fragment including 294 base pairs between the 2538th nucleotide from the start codon of aceE gene and the 62nd nucleotide in the downstream of the stop codon. In addition, primers, which were designed to have an SpeI restriction enzyme recognition site at a 5' end of the fragment and an XbaI restriction enzyme recognition site at a 3' end of the fragment (SEQ ID NOs: 11 and 12), were used to perform a PCR to obtain a DNA fragment including 294 base pairs between the 69th nucleotide in the downstream of the aceE gene stop codon and the 362nd nucleotide. PfuUltra™ High-Fidelity DNA Polymerase (Stratagene) was used as a polymerase, and a PCR was performed with 30 cycles of denaturing at 95° C. for 30 seconds; annealing at 55° C. for 30 seconds; and polymerization at 72° C. for 30 seconds and then polymerization at 72° C. for 7 minutes.

The two PCR amplification products and a pDZ vector for chromosomal introduction that had already been prepared by cleaving with an XbaI restriction enzyme were cloned by using an In-fusion Cloning Kit (TAKARA, JP) to prepare a pDZ-aceE2 vector.

```
SEQ ID NO: 9: aceE-P4F
5'-ccggggatcctctagaggtcccaggcgactacacc-3'

SEQ ID NO: 10: aceE-P4R
5'-gagctactagtacgacgaatcccgccgccagacta-3'

SEQ ID NO: 11: aceE-P5F
5'-gtcgtactagtagctcttttttagccgaggaacgcc-3'

SEQ ID NO: 12: aceE-P5R
5'-gcaggtcgactctagacatgctgttggatgagcac-3'
```

To obtain a promoter fragment of a *Corynebacterium glutamicum*-derived aceA gene, primers, which were designed to have an SpeI restriction enzyme recognition site at a 5' end and at a 3' end of the fragment (SEQ ID NOs: 13 and 14), were synthesized. The PCR was performed using the chromosomal DNA of *Corynebacterium glutamicum* KCCM11016P as a template and the synthesized primers to amplify a promoter region of about 500 base pairs being represented by a nucleotide sequence of SEQ ID NO: 1. The PCR amplification product and a DNA fragment that was obtained by treating a pDZ-aceE2 vector with SpeI restriction enzyme were cloned by using an In-fusion Cloning Kit (TAKARA, JP) to prepare a pDZ-aceE2-PaceA vector.

```
SEQ ID NO: 13: PaceA-P6F
5'-aaaaagagctactagtagcactctgactacctctg-3'

SEQ ID NO: 14: PaceA-P6R
5'-gattcgtcgtactagtttcctgtgcggtacgtggc-3'
```

Example 3: Preparation of Strains in Which aceA Gene Promoter is Inserted to Downstream of aceE Gene The pDZ-aceE1-PaceA and pDZ-aceE2-PaceA vectors prepared in Example 2 were introduced respectively by electric pulsing into *Corynebacterium glutamicum* KCCM11016P that is an L-lysine-producing strain (transformation method described in Van der Rest et al., Appl Microbiol Biotechnol, 52:541-545, 1999). The respective strains in which an aceA gene promoter was inserted into the downstream of the aceE gene stop codon on the chromosome so that the transcription from this promoter may occur in a direction opposite to the original direction were selected by performing a PCR to obtain an L-lysine-producing strain. The selected strains were named as *Corynebacterium glutamicum* KCCM11016P::aceE1-PaceA, and as *Corynebacterium glutamicum* KCCM11016P::aceE2-PaceA, respectively. *Corynebacterium glutamicum* KCCM11016P::aceE1-PaceA was internationally deposited in the name of *Corynebacterium glutamicum* CA01-2271 to Korean Culture Center of Microorganism (KCCM) on Jun. 12, 2013 with Accession Number KCCM11432P. The prepared strains were verified that the nucleotide sequence of target region obtained was analyzed by performing a PCR using SEQ ID NO: 3 and SEQ ID NO: 6 as primers for KCCM11016P::aceE1-PaceA, and SEQ ID NO: 9 and SEQ ID NO: 12 for as primers for KCCM11016P::aceE2-PaceA.

Example 4: Comparison of Lysine Productivity of Strains in Which aceA Gene Promoter is Inserted to Downstream of aceE Gene

*Corynebacterium glutamicum* KCCM11016P strain which was used as a parent strain, and *Corynebacterium glutamicum* KCCM11016P::aceE1-PaceA and *Corynebacterium glutamicum* KCCM11016P::aceE2-PaceA which were the L-lysine-producing strains prepared in Example 3 were cultured by the method described below.

*Corynebacterium glutamicum* KCCM11016P KCCM11016P::aceE1-PaceA, and KCCM11016P::aceE2-PaceA were inoculated respectively to 25 ml of the seed medium described below in 250 ml corner-baffled flasks, followed by shaking culture at 200 rpm at 30° C. for 20 hours. 1 ml of the seed culture solution was added to a 250 ml corner-baffled flask including 24 ml of the production medium described below, followed by shaking culture at 200 rpm at 30° C. for 72 hours. The respective compositions of the seed medium and the production mediums are described below.

<Seed Medium (pH 7.0)>
glucose 20 g, peptone 10 g, yeast extract 5 g, urea 1.5 g, a $KH_2PO_4$ 4 g, $K_2HPO_4$ 8 g, $MgSO_4 \cdot 7(H_2O)$ 0.5 g, biotin 100 µg, thiamine HCl 1000 µg, calcium pantothenate 2000 µg, nicotinamide 2000 µg (with reference to 1 L of distilled water).

<Production Medium (pH 7.0)>
glucose 100 g, $(NH_4)_2SO_4$ 40 g, soy protein 2.5 g, corn steep solids 5 g, urea 3 g, $KH_2PO_4$ 1 g, $MgSO_4 \cdot 7(H_2O)$ 0.5 g, biotin 100 µg, thiamine HCl 1000 µg, calcium pantothenate 2000 µg, nicotinamide 3000 µg, $CaCO_3$ 30 g (with reference to 1 L of distilled water).

After the culturing, the L-lysine concentration was measured using HPLC. When acetate was not added, the L-lysine concentration in the culture solutions of *Corynebacterium glutamicum* KCCM11016P, KCCM11016P::aceE1-PaceA, and KCCM11016P::aceE2-PaceA is shown in Table 1.

TABLE 1

Variation of L-lysine production (acetate not added)

| | Lysine (g/L) | | |
|---|---|---|---|
| Strain | Batch 1 | Batch 2 | Batch 3 |
| KCCM11016P | 43.5 | 43.1 | 43.4 |
| KCCM11016P::aceE1-PaceA | 43.7 | 43.2 | 43.6 |
| KCCM11016P::aceE2-PaceA | 43.3 | 43.4 | 43.7 |

In addition, the strains were cultured by the same method except that 5 g/L of acetate was added to the production medium to compare the L-lysine production. The L-lysine concentration in the culture solutions is shown in Table 2.

TABLE 2

Variation of L-lysine production (5 g/L of acetate added)

| | Lysine (g/L) | | |
|---|---|---|---|
| Strain | Batch 1 | Batch 2 | Batch 3 |
| KCCM11016P | 45.6 | 45.3 | 45.8 |
| KCCM11016P::aceE1-PaceA | 47.2 | 47.1 | 47.4 |
| KCCM11016P::aceE2-PaceA | 46.7 | 46.5 | 47.0 |

As shown in Table 1, in the absence of acetate, the L-lysine productivity of KCCM11016P::aceE1-PaceA and KCCM11016P::aceE2-PaceA strains was not different from that of the parent strain KCCM11016P.

However, as shown in Table 2, in the presence of acetate, the L-lysine productivity of the KCCM11016P::aceE1-PaceA strain was over 3.6% higher than that of the parent strain KCCM11016P, and that of the KCCM11016P::aceE2-PaceA strain was over 2.5% higher than that of the parent strain KCCM11016P.

In addition, comparison of the KCCM11016P::aceE1-PaceA strain and the KCCM11016P::aceE2-PaceA strain shows that the L-lysine production of the KCCM11016P::aceE1-PaceA strain in which the aceA promoter was inserted to the upstream of the aceE gene transcription terminator, which was between the stop codon and the upstream of the transcription terminator, was more effective. It indicates that the region between the stop codon and the upstream of the transcription terminator may be used to inhibit gene expression more effectively.

Example 5: Preparation of pDZ-aceE-Ppta Vector for Inhibiting aceE Gene Expression Acetate kinase (ackA, NCgl2656) and phosphotransacetylase (pta, NCgl2657), which are enzymes that are involved in an acetate metabolic process, form an operon, and the expression thereof is strengthened in the presence of acetate. Therefore, when the promoters of the genes are used, the expression of a gene may be specifically induced in the presence of acetate.

In Example 5, to inhibit the expression of the aceE gene in the presence of acetate, a vector for using a pta-ack operon promoter that was the pta gene upstream promoter region was prepared.

To inhibit the expression of the aceE gene, a vector which may comprise a pta gene promoter in the downstream of the aceE gene stop codon, which is between the stop codon and the upstream of the transcription terminator, was constructed so that the transcription from pta gene promoter may occur in a direction opposite to the original direction of the aceE gene transcription.

To obtain a fragment of a *Corynebacterium glutamicum*-derived aceE gene, the chromosomal DNA of *Corynebacterium glutamicum* KCCM11016P was used as a template to prepare a pDZ-aceE1 vector by the same method as Example 2.

To obtain a promoter fragment of a *Corynebacterium glutamicum*-derived pta gene, primers, which were designed to have an SpeI restriction enzyme recognition site at a 5' end and at a 3' end of the fragment (SEQ ID NO: 15 and SEQ ID NO: 16), were synthesized. The chromosomal DNA of *Corynebacterium glutamicum* KCCM11016P as a template, and the synthesized primers were used to perform a PCR to amplify a promoter region of about 340 base pairs being represented by a nucleotide sequence of SEQ ID NO: 2. The PCR amplification product and a DNA fragment that was obtained by treating a pDZ-aceE1 vector with a SpeI restriction enzyme were cloned by using an In-fusion Cloning Kit (TAKARA, JP) to prepare a pDZ-aceE1-Ppta vector.

```
SEQ ID NO: 15: Ppta-P7F
5'-gtcccttgagactagtctttgctggggtcagatttg-3'

SEQ ID NO: 16: Ppta-P7R
5'-ctgaggaataactagtacatcgcctttctaatttc-3'
```

Example 6: Preparation of Strains in Which pta Gene Promoter is Inserted to Downstream of aceE Gene and Comparison of Lysine Productivity Thereof The *Corynebacterium glutamicum* KCCM11016P was transformed with the pDZ-aceE1-Ppta vector prepared in Example 5 by the same method as Example 3. The strain in which a pta gene promoter was inserted to the downstream of the aceE gene stop codon on the chromosome so that the transcription may occur in a direction opposite to the original direction of the aceE gene transcription was selected by performing a PCR to obtain an L-lysine-producing strain, which was named as KCCM11016P::aceE1-Ppta. The prepared KCCM11016P::aceE1-Ppta strain was verified that the nucleotide sequence of target region obtained was analyzed by performing a PCR using SEQ ID NO: 3 and SEQ ID NO: 6 as primers.

The prepared strain was cultured by the same method as Example 4, and the concentration of L-lysine recovered from the culture solution was measured. When acetate was not added, the L-lysine concentration in the culture solution is shown in Table 3.

TABLE 3

Variation of L-lysine production (acetate not added)

| | Lysine (g/L) | | |
|---|---|---|---|
| Strain | Batch 1 | Batch 2 | Batch 3 |
| KCCM11016P | 42.9 | 43.5 | 43.4 |
| KCCM11016P::aceE1-Ppta | 43.2 | 43.3 | 43.6 |

In addition, the strain was cultured by the same method except that 5 g/L of acetate was added to the production medium to compare the L-lysine production. The L-lysine concentration in the culture solution is shown in Table 4.

TABLE 4

Variation of L-lysine production (5 g/L of acetate added)

| | Lysine (g/L) | | |
|---|---|---|---|
| Strain | Batch 1 | Batch 2 | Batch 3 |
| KCCM11016P | 45.5 | 45.7 | 45.3 |
| KCCM11016P::aceE1-Ppta | 46.7 | 46.5 | 46.6 |

As shown in Table 3, in the absence of acetate, the L-lysine productivity of the KCCM11016P::aceE1-Ppta strain was not different from that of the parent strain KCCM11016P.

However, as shown in Table 4, in the presence of acetate, the L-lysine productivity of the KCCM11016P::aceE1-Ppta strain was over 2.4% higher than that of the parent strain KCCM11016P.

In addition, since the L-lysine productivity of the KCCM11016P::aceE1-PaceA strain was higher than that of the KCCM11016P::aceE1-Ppta strain, in the presence of acetate, the expression of a target gene may be inhibited more effectively by using the aceA gene promoter than by using the pta gene promoter.

Example 7: Preparation of Strains in Which aceA Gene Promoter is Inserted to Downstream of aceE Gene Three L-lysine-producing strains which were *Corynebacterium glutamicum* KFCC10750, KCCM10770P, and CJ3P were transformed respectively with the pDZ-aceE1-PaceA vector prepared in Example 2 by the same method as Example 3. The strains in which an aceA gene promoter was inserted to the downstream of the aceE gene stop codon on the chromosome so that the transcription may occur in a direction opposite to the original direction of the aceE gene transcription was selected by performing a PCR. The obtained three L-lysine-producing strains were KFCC10750::aceE1-PaceA, KCCM10770P::aceE1-PaceA, and CJ3P::aceE1-PaceA. The prepared strains were verified that the nucleotide sequence of target region obtained was analyzed by performing a PCR using SEQ ID NO: 3 and SEQ ID NO: 6 as primers.

The prepared strains were cultured by the same method as Example 4, and the concentration of L-lysine recovered from the culture solutions was measured. When acetate was not added, the L-lysine concentration in the culture solutions is shown in Table 5.

TABLE 5

Variation of L-lysine production (acetate not added)

| | Lysine (g/L) | | |
|---|---|---|---|
| Strain | Batch 1 | Batch 2 | Batch 3 |
| KFCC10750 | 38.3 | 38.0 | 38.4 |
| KFCC10750::aceE1-PaceA | 38.6 | 38.2 | 38.3 |
| KCCM10770P | 47.5 | 47.3 | 47.6 |
| KCCM10770P::aceE1-PaceA | 47.3 | 47.7 | 47.5 |
| CJ3P | 8 | 8.4 | 8.3 |
| CJ3P::aceE1-PaceA | 8.2 | 8.1 | 8.5 |

In addition, the strains were cultured by the same method except that 5 g/L of acetate was added to the production medium to compare the L-lysine production. The L-lysine concentration in the culture solutions is shown in Table 6.

TABLE 6

Variation of L-lysine production (5 g/L of acetate added)

| | Lysine (g/L) | | |
|---|---|---|---|
| Strain | Batch 1 | Batch 2 | Batch 3 |
| KFCC10750 | 39.3 | 39.5 | 39.2 |
| KFCC10750::aceE1-PaceA | 41.3 | 41.6 | 41.0 |
| KCCM10770P | 47.5 | 47.3 | 47.6 |
| KCCM10770P::aceE1-PaceA | 49.0 | 48.6 | 48.8 |
| CJ3P | 8 | 8.4 | 8.3 |
| CJ3P::aceE1-PaceA | 9.5 | 9.7 | 9.4 |

As shown in Table 5, in the absence of acetate, the L-lysine productivity of the three KFCC10750::aceE1-PaceA, KCCM10770P::aceE1-PaceA, CJ3P::aceE1-PaceA strains was not different from that of the parent strain.

However, as shown in Table 6, in the presence of acetate, the L-lysine productivity of the KFCC10750::aceE1-PaceA strain was 5% higher than that of the parent strain, that of the KCCM10770P::aceE1-PaceA strain was 2.8% higher than that of the parent strain, and that of the CJ3P::aceE1-PaceA strain was 15% higher than that of the parent strain.

Example 8: Preparation of Vector for Inhibiting hom Gene Expression

L-threonine biosynthetic pathway using a same substrate as L-lysine biosynthetic pathway may be weakened to increase L-lysine productivity. An example of the methods of weakening L-threonine biosynthetic pathway is to decrease the enzymatic activity of homoserine dehydrogenase (hom, NCgl1136) which produces homoserine from aspartate.

In Corynebacterium glutamicum, the hom gene forms hom-thrB operon with thrB gene, and the transcription terminator of the hom gene exists in the downstream of the thrB gene. It was reported that a promoter exists in the upstream of the hom-thrB operon that is the upstream of the hom gene. In addition, it was reported a second promoter exists in the upstream of the thrB gene operon (Mateos et al., J Bacteriol, 176:7362-7371, 1994). Therefore, an aceA gene promoter was inserted to the downstream of the hom gene stop codon so that the trascription from this promoter may occur in a direction opposite to the original direction of the hom gene transcription in order to selectively inhibit the expression of the hom gene in the presence of acetate. To maintain the expression of the thrB gene, a second promoter sequence was added to the upstream of thrB gene ORF.

In Example 8, a recombinant vector was prepared by inserting an aceA gene promoter between the downstream of the hom gene stop codon and the upstream of the thrB gene.

To obtain a fragment of a Corynebacterium glutamicum-derived hom gene, the chromosomal DNA of Corynebacterium glutamicum KCCM11016P was used as a template, and primers, which were designed to have an XbaI restriction enzyme recognition site at a 5' end of the fragment and an SpeI restriction enzyme recognition site at a 3' end of the fragment (SEQ ID NOs: 17 and 18), were synthesized. A PCR was performed using the synthesized primers to obtain a DNA fragment including 300 base pairs between the 1039th nucleotide from the hom gene start codon and the 1338th nucleotide which was a stop codon. Even when an aceA is inserted between the hom-thrB operons, the expression of the thrB gene should be maintained. Therefore, when the DNA fragment including the 300 base pairs of the hom gene stop codon downstream was prepared, primers which were designed to further add a thrB promoter sequence of 32 base pairs to a 5' side (SEQ ID NOs: 19 and 20) were synthesized. A PCR was performed using these primers (SEQ ID NOs: 19 and 20) to obtain a DNA fragment of 334 base pairs having an SpeI restriction enzyme recognition site at a 5' end of the fragment and an XbaI restriction enzyme recognition site at a 3' end of the fragment. The PCR was performed under the same conditions as Example 2.

The two PCR amplification products and a pDZ vector for chromosomal introduction that had already been prepared by cleaving with an XbaI restriction enzyme were cloned by using an In-fusion Cloning Kit (TAKARA, JP) to prepare a pDZ-hom vector.

```
SEQ ID NO: 17: hom-h1F
5'-ccgggatcctctagaccaggtgagtccacctacg-3'

SEQ ID NO: 18: hom-h1R
5'-gaggcggatcactagtttagtcccttcgaggcgg-3'

SEQ ID NO: 19: hom-h2F
5'-actagtgatccgcctcgaaagggac-3'

SEQ ID NO: 20: hom-h2R
5'-gcaggtcgactctagagactgcggaatgttgttgtg-3'
```

To obtain a promoter fragment of a Corynebacterium glutamicum-derived aceA gene, primers which were designed to have an SpeI restriction enzyme recognition site at a 5' end and at a 3' end of the fragment (SEQ ID NOs: 21 and 22) were synthesized. The PCR was performed using the chromosomal DNA of *Corynebacterium glutamicum* KCCM11016P as a template, and the synthesized primers to amplify a promoter region of about 500 base pairs being represented by a nucleotide sequence of SEQ ID NO: 1. The PCR amplification product and a DNA fragment that was obtained by treating a pDZ-hom vector with a SpeI restriction enzyme were cloned by using an In-fusion Cloning Kit (TAKARA, JP) to prepare a pDZ-hom-PaceA vector.

```
SEQ ID NO: 21: PaceA-h3F
5'-gaggcggatcactagtagcactctgactacctctg-3'

SEQ ID NO: 22: PaceA-h3R
5'-aagggactaaactagtttcctgtgcggtacgtggc-3'
```

Example 9: Preparation of Strains to Which aceA Gene Promoter is Inserted to Downstream of hom Gene and Comparison of Lysine Productivity Thereof The *Corynebacterium glutamicum* KCCM11016P that is an L-lysine-producing strain was transformed with the pDZ-hom-PaceA vector prepared in Example 8 by the same method as Example 3. The strain in which an aceA gene promoter was inserted to the downstream of the hom gene stop codon on the chromosome so that the transcription may occur in a direction opposite to the original direction of the hom gene transcription was selected by performing a PCR to obtain an L-lysine-producing strain, which was named as KCCM11016P::hom-PaceA. The prepared KCCM11016P::hom-PaceA strain was verified that the nucleotide sequence of target region obtained was analyzed by performing a PCR using SEQ ID NO: 17 and SEQ ID NO: 20 as primers.

The *Corynebacterium glutamicum* KCCM11016P strain which was used as a parent strain and the prepared KCCM11016P::hom-PaceA strain were cultured by the same method as Example 4, and the concentration of L-lysine recovered from the culture solutions was measured. When acetate was not added, the L-lysine concentration in the culture solutions of the *Corynebacterium glutamicum* KCCM11016P strain and the KCCM11016P::hom-PaceA is shown in Table 7.

TABLE 7

Variation of L-lysine production (acetate not added)

| Strain | Lysine (g/L) | | |
|---|---|---|---|
|  | Batch 1 | Batch 2 | Batch 3 |
| KCCM11016P | 43.2 | 43.3 | 43.6 |
| KCCM11016P::hom-PaceA | 43.3 | 43.6 | 43.4 |

In addition, the strains were cultured by the same method except that 5 g/L of acetate was added to the production medium to compare the L-lysine production. The L-lysine concentration in the culture solutions is shown in Table 8.

TABLE 8

Variation of L-lysine production (5 g/L of acetate added)

| Strain | Lysine (g/L) | | |
|---|---|---|---|
|  | Batch 1 | Batch 2 | Batch 3 |
| KCCM11016P | 44.9 | 45.6 | 45.2 |
| KCCM11016P::hom-PaceA | 46.3 | 46.6 | 46.4 |

As shown in Table 7, in the absence of acetate, the L-lysine productivity of the KCCM11016P::hom-PaceA strain was not different from that of the parent strain KCCM11016P.

However, as shown in Table 8, in the presence of acetate, the L-lysine productivity of the KCCM11016P::hom-PaceA strain was over 2.6% higher than that of the parent strain KCCM11016P.

Example 10: Preparation of Vector for Inhibiting murE Gene Expression

UDP-N-acetylmuramoylalanyl-D-glutamate-2,6-diaminopimelate ligase (murE, NCgl2083) uses meso-2,6-diaminopimelate, which is a precursor for lysine biosynthesis, in somatic synthesis. Weakening of the murE gene activity may decrease the inflow of carbon sources to somatic synthesis and increase the inflow of carbon sources to a lysine biosynthetic pathway to increase lysine production.

In *Corynebacterium glutamicum*, the murE gene (NCgl2083) forms an operon with seven genes from NCgl2076 to NCgl2082. The transcription of the operon starts from the NCgl2083 murE in the direction of the NCgl2076 gene. So, a transcription terminator exists in the downstream of the NCgl2076 gene. Therefore, an aceA gene promoter was inserted to the downstream of the murE gene stop codon so that the transcription may occur in a direction opposite to the original direction of the murE gene transcription in order to selectively inhibit the expression of the murE gene in the presence of acetate. To maintain the expression of the other seven genes except the murE gene which is located in the first region of the operon, a murE operon promoter was further added to the upstream of the NCgl2082 gene ORF.

In Example 10, a recombinant vector was prepared by inserting an aceA gene promoter to the downstream of the murE gene stop codon.

To obtain a fragment of a *Corynebacterium glutamicum*-derived murE gene, the chromosomal DNA of *Corynebacterium glutamicum* KCCM11016P was used as a template, and primers, which were designed to have an XbaI restriction enzyme recognition site at a 5' end of the fragment and an XhoI restriction enzyme recognition site at a 3' end of the fragment (SEQ ID NOs: 23 and 24), were synthesized. A PCR was performed using the synthesized primers to obtain a DNA fragment including 300 base pairs between the 1267th nucleotide from the murE gene start codon and the 1566th nucleotide which was a stop codon. In addition, primers, which were designed to have an XhoI restriction enzyme recognition site at a 5' end of the fragment and an XbaI restriction enzyme recognition site at a 3' end of the fragment (SEQ ID NOs: 25 and 26), were synthesized. A PCR was performed using the synthesized primers to obtain a DNA fragment including 292 base pairs from the 10th nucleotide in the downstream of the murE gene stop codon. The PCR was performed under the same conditions as Example 2. The two PCR amplification products and a pDZ vector for chromosomal introduction that had already been prepared by cleaving with an XbaI restriction enzyme were cloned by using an In-fusion Cloning Kit (TAKARA, JP) to prepare a pDZ-murE vector.

```
SEQ ID NO: 23: mur-m1F
5'-ccggggatcctctagaaaccctcgttcagaggtgc-3'
```

-continued

```
SEQ ID NO: 24: mur-m1R
5'-ttgtgatcatctcgagctatccttcttccgtagtaag-3'

SEQ ID NO: 25: mur-m2F
5'-ag ctcgagatgatcacaatgacccttgg-3'

SEQ ID NO: 26: mur-m2R
5'-gcaggtcgactctagacatgagcataaatgtcagc-3'
```

To obtain a fragment of a *Corynebacterium glutamicum*-derived aceA gene, primers, which were designed to have an XhoI restriction enzyme recognition site at a 5' end of the fragment (SEQ ID NOs: 27 and 28), were synthesized. The chromosomal DNA of *Corynebacterium glutamicum* KCCM11016P as a template, and the synthesized primers were used to perform a PCR to amplify a promoter region of about 500 base pairs being represented by a base sequence of SEQ ID NO: 1. In addition, to obtain a promoter region of a *Corynebacterium glutamicum*-derived murE operon, the chromosomal DNA of *Corynebacterium glutamicum* KCCM11016P was used as a template, and primers, which were designed to have an XhoI restriction enzyme recognition site at a 3' end of the fragment (SEQ ID NOs: 29 and 30), were synthesized. A PCR was performed using the synthesized primers to obtain a DNA fragment including 300 base pairs in the upstream of murE gene ORF.

The two PCR amplification products and the DNA fragment obtained by treating the pDZ-murE vector with XhoI restriction enzyme were cloned by using an In-fusion Cloning Kit (TAKARA, JP) to prepare a pDZ-murE-PaceA-PmurE vector.

```
SEQ ID NO: 27: mur-m3F
5'-tcatcagcagcactctgactacctctg-3'

SEQ ID NO: 28: mur-m3R
5'-agaaggatagctcgagttcctgtgcggtacgtggc-3'

SEQ ID NO: 29: mur-m4F
5'-agagtgctgctgatgatcctcgatttg-3'

SEQ ID NO: 30: mur-m4R
5'-ttgtgatcatctcgagggttttctctcctccacagg-3'
```

Example 11: Preparation of Strains to Which aceA Gene Promoter is Inserted to Downstream of murE Gene and Comparison of Lysine Productivity Thereof The *Corynebacterium glutamicum* KCCM11016P was transformed with the pDZ-murE-PaceA-PmurEvector prepared in Example 10 by the same method as Example 3.

The strain in which an aceA gene promoter was inserted to the downstream of the murE gene stop codon on the chromosome so that the transcription may occur in a direction opposite to the original direction of the murE gene transcription was selected by performing a PCR to obtain an L-lysine-producing strain, which was named as KCCM11016P::murE-PaceA-PmurE. The prepared KCCM11016P::murE-PaceA-PmurE strain was verified that the nucleotide sequences of target region obtained was analyzed by performing a PCR using SEQ ID NO: 23 and SEQ ID NO: 26 as primers.

The *Corynebacterium glutamicum* KCCM11016P strain which was used as a parent strain and the prepared KCCM11016P::murE-PaceA-PmurE strain were cultured by the same method as Example 4, and the concentration of L-lysine recovered from the culture solutions was measured.

When acetate was not added, the L-lysine concentration in the culture solutions of the *Corynebacterium glutamicum* KCCM11016P strain and the KCCM11016P::murE-PaceA-PmurE strain is shown in Table 9.

TABLE 9

Variation of L-lysine production (acetate not added)

| | Lysine (g/L) | | |
|---|---|---|---|
| Strain | Batch 1 | Batch 2 | Batch 3 |
| KCCM11016P | 43.5 | 43.9 | 44.0 |
| KCCM11016P::murE-PaceA-PmurE | 43.7 | 44.1 | 43.8 |

In addition, the strains were cultured by the same method except that 5 g/L of acetate was added to the production medium to compare the L-lysine production. The L-lysine concentration in the culture solutions is shown in Table 10.

TABLE 10

Variation of L-lysine production (5 g/L of acetate added)

| | Lysine (g/L) | | |
|---|---|---|---|
| Strain | Batch 1 | Batch 2 | Batch 3 |
| KCCM11016P | 45.2 | 45.6 | 45.3 |
| KCCM11016P::murE-PaceA-PmurE | 46.6 | 46.9 | 46.5 |

As shown in Table 9, in the absence of acetate, the L-lysine productivity of the KCCM11016P::murE-PaceA-PmurE strain was not different from that of the parent strain KCCM11016P.

However, as shown in Table 10, in the presence of acetate, the L-lysine productivity of the KCCM11016P::murE-PaceA-PmurE strain was over 2.8% higher than that of the parent strain KCCM11016P.

Example 12: Preparation of Vector for Inhibiting dapA Gene Expression

L-lysine biosynthetic pathway using the same substrate as L-threonine biosynthetic pathway may be weakened to increase L-threonine productivity. An example of the methods of weakening L-lysine biosynthetic pathway is to decrease the enzymatic activity of dihydrodipicolinate synthase (dapA, NCgl1896) which is involved in the production of lysine from aspartate.

In *Corynebacterium glutamicum*, the dapA gene forms dapA-ORF4 operon with ORF4 (NCgl1895) gene, and thus the transcription terminator of the dapA gene exists in the downstream of the ORF4 gene. In addition, it was reported that a promoter exists in the upstream of the dapA-ORF4 operon that is the upstream of the dapA gene, and a second promoter exists in the upstream of the ORF4 gene (Patek et al., Biotechnology letters, 19:1113-1117, 1997). Therefore, an aceA gene promoter was inserted to the downstream of the dapA gene stop codon so that the transcription may occur in a direction opposite to the original direction of the dapA gene transcription in order to selectively inhibit the expression of the dapA gene in the presence of acetate. To maintain the expression of the ORF4 gene, a promoter region sequence of about 100 base pairs in the ORF4 gene upstream was added to the ORF upstream of the ORF4 gene.

In Example 12, a recombinant vector was prepared by inserting an aceA gene promoter to the downstream of the dapA gene stop codon.

To obtain a fragment of a *Corynebacterium glutamicum*-derived dapA gene, the chromosomal DNA of *Corynebacterium glutamicum* KCCM11016P was used as a template, and primers, which were designed to have an XbaI restriction enzyme recognition site at a 5' end of the fragment and an SpeI restriction enzyme recognition site at a 3' end of the fragment (SEQ ID NOs: 31 and 32), were synthesized. A PCR was performed using the synthesized primers to obtain a DNA fragment including 301 base pairs between the 606th nucleotide from the dapA gene start codon and the 906th nucleotide which was a stop codon. In addition, primers, which were designed to have an SpeI restriction enzyme recognition site at a 5' end of the fragment and an XbaI restriction enzyme recognition site at a 3' end of the fragment (SEQ ID NOs: 33 and 34), were synthesized. Through a PCR, a DNA fragment which further includes a promoter region sequence of about 100 base pairs between the 809th nucleotide from the dapA gene start codon and the 2nd nucleotide in the stop codon downstream, to maintain the expression of the ORF4 gene, and 213 base pairs in the dapA gene stop codon downstream was obtained. The PCR was performed under the same conditions as Example 2. The two PCR amplification products and a pDZ vector for chromosomal introduction that had already been prepared by cleaving with an XbaI restriction enzyme were cloned by using an In-fusion Cloning Kit (TAKARA, JP) to prepare a pDZ-dapA vector.

```
SEQ ID NO: 31: dapA-d1F
5'-ccggggatcctctaga tgtttggcttgctttgggc-3'

SEQ ID NO: 32: dapA-d1R
5'-gttgatgcactagtttatagaactccagcttt-3'

SEQ ID NO: 33: dapA-d2F
5'-ttctataaactagtgcatcaacgtaggagatcc-3'

SEQ ID NO: 34: dapA-d2R
5'-gcaggtcgactctagacgttctgggaaccctgag-3'
```

To obtain a promoter fragment of a *Corynebacterium glutamicum*-derived aceA gene, primers, which were designed to have an SpeI restriction enzyme recognition site at a 5' end and at a 3' end of the fragment (SEQ ID NOs: 35 and 36), were synthesized. The PCR was performed using the chromosomal DNA of *Corynebacterium glutamicum* KCCM11016P as a template and the synthesized primers to amplify a promoter region of about 500 base pairs being represented by a nucleotide sequence of SEQ ID NO: 1. The PCR amplificated product and a DNA fragment, which was obtained by treating a pDZ-dapA vector with a SpeI restriction enzyme, were cloned by using an In-fusion Cloning Kit (TAKARA, JP) to prepare a pDZ-dapA-PaceA vector.

```
SEQ ID NO: 35: PaceA-d3F
5'-acgttgatgc actagt agcactctgactacctctg-3'

SEQ ID NO: 36: PaceA-d3R
5'-agttctataa actagt ttcctgtgcggtacgtggc-3'
```

Example 13: Preparation of Strains in Which aceA Gene Promoter is Inserted to Downstream of dapA Gene and Comparison of Threonine Productivity Thereof To verify the effect of inhibiting the dapA gene expression in an L-threonine-producing strain, the pDZ-dapA-PaceA vector prepared in Example 12 was transformed by the same method as Example 3 into a *Corynebacterium glutamicum* KCCM11222P (Korean Patent NO: 2013-0061570) strain that is an L-threonine-producing strain. The strain in which an aceA gene promoter was inserted to the downstream of the dapA gene stop codon on the chromosome so that the transcription may occur in a direction opposite to the original direction of the dapA gene transcription was selected by performing a PCR, which was named as KCCM11222P::dapA-PaceA. The prepared KCCM11222P::dapA-PaceA strain was verified that the nucleotide sequence of target region obtained was analyzed by performing a PCR by using SEQ ID NO: 31 and SEQ ID NO: 34 as primers.

The *Corynebacterium glutamicum* KCCM11222P strain, which was used as a parent strain, and the prepared KCCM11222P::dapA-PaceA strain were cultured by the method described below.

Each of the strains was respectively inoculated 25 ml of a seed medium in 250 ml corner-baffled flasks, followed by shaking culture at 200 rpm at 30° C. for 20 hours. Afterward, 1 ml of the seed culture solution was added to a 250 ml corner-baffled flask including 24 ml of a production medium, followed by shaking culture at 200 rpm at 30° C. for 48 hours at 200 rpm. The respective compositions of the seed medium and the production mediums are described below.

<Seed Medium (pH 7.0)> glucose 20 g, peptone 10 g, yeast extract 5 g, urea 1.5 g, $KH_2PO_4$ 4 g, $K_2HPO_4$ 8 g, $MgSO_4.7(H_2O)$ 0.5 g, biotin 100 μg, thiamine HCI 1000 μg, calcium pantothenate 2000 μg, nicotinamide 2000 μg (with reference to 1 L of distilled water).

<Production Medium (pH 7.0)> glucose 100 g, $(NH_4)_2SO_4$ 20 g, soy protein 2.5 g, corn steep solids 5 g, urea 3 g, $KH_2PO_4$ 1 g, $MgSO_4.7(H_2O)$ 0.5 g, biotin 100 μg, thiamine HCI 1000 μg, calcium pantothenate 2000 μg, nicotinamide 3000 μg, $CaCO_3$ 30 g (with reference to 1 L of distilled water).

After the culturing, L-threonine concentration in the culture solution was measured by HPLC. When acetate was not added, the L-threonine concentration in the culture solutions of *Corynebacterium glutamicum* KCCM11222P and KCCM11222P::dapA-PaceA is shown in Table 11.

TABLE 11

Variation of L-threonine production (acetate not added)

| | Threonine (g/L) | | |
|---|---|---|---|
| Strain | Batch 1 | Batch 2 | Batch 3 |
| KCCM11222P | 7.0 | 6.9 | 7.2 |
| KCCM11222P::dapA-PaceA | 7.1 | 7.3 | 7.0 |

In addition, the strains were cultured by the same method except that 5 g/L of acetate was added to the production medium to compare the L-threonine production. The L-threonine concentration in the culture solutions is shown in Table 12.

TABLE 12

Variation of L-threonine production (5 g/L of acetate added)

| | Threonine (g/L) | | |
|---|---|---|---|
| Strain | Batch 1 | Batch 2 | Batch 3 |
| KCCM11222P | 7.6 | 7.4 | 7.7 |
| KCCM11222P::dapA-PaceA | 11.2 | 11.5 | 11.4 |

As shown in Table 11, in the absence of acetate, the L-threonine productivity of the KCCM11222P::dapA-PaceA strain was not different from that of the parent strain KCCM11222P.

However, as shown in Table 12, in the presence of acetate, the L-threonine productivity of the KCCM11222P::dapA-PaceA strain was over 50% higher than that of the parent strain KCCM11222P.

ACCESSION NUMBER

Research Center Name: Korean Collection for Type Cultures (International)
Accession Number: KCCM11432P
Accession Date: Jun. 12, 2013

As described above, according to the one or more of the above embodiments of the present invention, an acetate-inducible promoter may be used to effectively produce L-amino acids, since a target L-amino acid may be produced in a high yield by weakening the expression of a target gene by adding acetate at an appropriate time.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of producing a target L-amino acids, the method comprising
culturing a recombinant coryneform microorganism in a medium, wherein the recombinant coryneform microorganism is capable of producing a target L-amino acid and is transformed by inserting an acetate-inducible promoter downstream of a stop codon of a target gene in a chromosome such that transcription from the acetate-inducible promoter occurs in a direction opposite to the direction of the target gene transcription, wherein the target gene is a gene located at a branch point of a biosynthetic pathway of the target L-amino acid and encoding an enzyme involved in byproduct production, wherein the target L-amino acid is L-threonine, L-methionine, L-isoleucine, L-lysine, L-alanine, or L-valine.

2. The method according to claim 1, wherein the downstream of the stop codon is between the stop codon and an upstream of a transcription terminator of the target gene.

3. The method according to claim 1, wherein the acetate-inducible promoter is a nucleotide sequence of SEQ ID NO: 1 or SEQ ID NO: 2.

4. The method according to claim 1, wherein the target gene is at least one gene selected from the group consisting of a gene encoding a pyruvate dehydrogenase subunit E1, a gene encoding homoserine dehydrogenase, and a gene encoding a UDP-N-acetylmuramoylalanyl-D-glutamate-2,6-diaminopimelate ligase; and the target L-amino acid is L-lysine.

5. The method according to claim 1, wherein the target gene is at least one gene selected from the group consisting of a gene encoding a pyruvate dehydrogenase subunit E1 and a gene encoding dihydrodipicolinate synthase; and the target L-amino acid is L-threonine.

6. The method according to claim 1, wherein the target gene is at least one gene selected from the group consisting of a gene encoding a pyruvate dehydrogenase subunit E1, a gene encoding homoserine dehydrogenase, a gene encoding a UDP-N-acetylmuramoylalanyl-D-glutamate-2,6-diaminopimelate ligase, a gene encoding a homoserine kinase, and a gene encoding dihydrodipicolinate synthase.

7. The method according to claim 1, further comprising adding acetate during the culturing to cause a transcription from the acetate-inducible promoter in a direction opposite to the direction of the target gene transcription so that RNA polymerase complexes conflict with each other to weaken the expression of the target gene, and to strengthen the target L-amino acid production capability of the recombinant coryneform microorganism.

* * * * *